United States Patent [19]

Sonenshein et al.

[11] Patent Number: 4,725,535

[45] Date of Patent: Feb. 16, 1988

[54] PROMOTER PROBE VECTORS

[76] Inventors: Abraham L. Sonenshein, 549 Washington St., Brookline, Mass. 02146; Caroline E. Donnelly, 15 Medford St., Arlington, Mass. 02174

[21] Appl. No.: 468,300

[22] Filed: Feb. 22, 1983

[51] Int. Cl.[4] .................. C12Q 1/68; C12P 19/34; C12N 15/00; C12N 1/00

[52] U.S. Cl. .......................................... 435/6; 435/91; 435/172.3; 435/320; 935/6; 935/41; 935/29; 935/82

[58] Field of Search ................. 435/6, 68, 172.3, 317; 935/6, 29, 41, 73, 74, 79, 82

[56] References Cited

PUBLICATIONS

An et al, "Plasmid Vehicles for Direct Cloning of *Escherichia Coli* Promoters", Journal of Bacteriology, 140(2), pp. 400–407 (1979).
Bibb et al, "Gene Expression in Streptomyces: Construction and Application of Promoter-Probe Plasmid Vectors in Streptomyces Lividans", Molecular and General Genetics, 187, pp. 265–277 (1982).
West et al, "Construction and Characterization of *E. Coli* Promoter-Probe Plasmid Vectors", Gene, 7, pp. 271–288 (1979).
Goldfarb et al., *Nature*, 293:309 (1981).
Williams et al., *J. Bact.*, 146:1162 (1981).
Davies et al, (I) *J. Mol. Biol.*, 36:413 (1968).
Davies et al, (II) *Advanced Bacterial Genetics* (Cold Spring Harbor, 1980).
Haldenwang et al, (I) *J. Bact.*, 142:90 (1980).
Haldenwang et al, (II) *Cell*, 23:615 (1981).
Malamy, *Cold Spring Harbor Symposium on Quantitative Biology*, 31:189 (1965).
Donnelly et al., *Molecular Cloning and Gene Regulations in Bacilli*, 63 (Acad. Press, Inc. 1982).
Cohen et al., *PNAS, U.S.A.*, 69:211 0 (1972).
Contente et al., *Molec. Gen. Genet.*, (Cold Spr. Harbor, 1972).
Miller, *Experiments in Molecular Genetics*, (Cold Spring Harbor, 1971).
Fisher et al., *Spores*, VI:226 (Am. Soc. Microbiol., 1975).
Gryczan et al., *J. Bact.*, 134:318 (1978).
Prestige et al., *Biochem. Biophys. Acta*, 100:591.
Copeland et al., *Bact. Rev.*, 32:301 (1968).
Sutcliffe et al., *Cold Spring Harbor Symposium on Quantitative Biology*, 43:77 (1979).
Hutchinson et al., *Gene*, 8:267 (1980).
Silverstone et al., *PNAS, U.S.A.*, 66:773 (1970).
Stuber et al., *PNAS, U.S.A.*, 78:167 (1981).
Caulfield et al., *J. Bact.*, 138:345 (1979).
Kilbane et al., *J. Mol. Biol.*, 143:73 (1980).
Chang et al., *Molecular Cloning and Gene Regulation in Bacilli* (Acad. Press, 1982).
Williams et al., *Gene*, 16:199 (1981).
Palva et al., *PNAS, U.S.A.*, 79:5582 (Sep. 1982).
Goldfarb et al., *PNAS, U.S.A.* (Oct. 1982).

*Primary Examiner*—J. E. Tarcza
*Attorney, Agent, or Firm*—David G. Conlin; Gregory D. Williams

[57] ABSTRACT

Promoter probe vectors for determining the presence of efficient promoter regions on DNA segments, which segments permit microbiological expression of genetic information. The promoter probe vector comprises replicons active in *E. coli* and *B. subtilis*, a structural gene for B-galactosidase and at least one endonuclease restriction site suitable for insertion of promoter-containing DNA fragments.

14 Claims, 2 Drawing Figures

PROMOTER PROBE VECTORS

BACKGROUND OF THE INVENTION

This invention relates to promoter probe vectors, which can be used for readily determining the presence of efficient promoter regions on DNA segments, which regions are effective in selected species of microorganisms to permit microbiological expression of genetic information. More particularly, the invention relates to promoter probe vectors, which are capable of providing easy identification of efficient promoters for expression of genes in *Bacillus subtilis* and *Escherichia coli*, as well as methods of making and using such vectors, and products made utilizing such vectors.

A primary basis of industrial utility of recombinant DNA inventions and developments is production of desired products by microorganisms which are normally unable to produce them. In this regard, much of the published literature concerning the application of genetic engineering techniques for the production of commercially valuble products, such as hormones, vaccines, enzymes and various polypeptides, involves use of *Escherichia coli* as the host, into which foreign genes are introduced. Nevertheless, many fermentation engineers consider *Bacillus subtilis* to be the bacterium of choice for industrial application of recombinant DNA technology because of the likelihood of increased yield and decreased toxicity of products made by recombinant *B. subtilis* organisms.

In *Escherichia coli* and other organisms, the use of operon fusions has proved to be a powerful tool for understanding gene regulation. Operon fusion is a technique where a gene coding for a desired product is fused to the regulatory region of a different gene operon, thereby using that operon's promoter region to cause expression of the desired product. Expression of a foreign gene in a given host often requires that that gene be transcribed from a promoter site indigenous to the host, a factor which has important ramifications for many practical applications of recombinant DNA technology.

At the present state of this technology, it is difficult if not impossible to predict which promoter segments will be operable in a given type of bacterium for expression of a given gene. Yet commercial scale use of the genetic information obtained through recombinant DNA techniques applied to *Escherichia coli* or other microorganisms may require means for obtaining efficient expression of a desired gene in a microorganism like *Bacillus subtilis*.

Until the present invention, location of promoters which permit efficient expression of target genes in *B. subtilis* has been a tedious, difficult procedure, with uncertain results. Those plasmids which have been utilized to achieve expression of foreign genes in *B. subtilis* have typically relied on expression of antibiotic resistance properties, and the techniques utilized to judge the efficiency of expression have involved growth measurement of the rDNA recipient microorganisms in the presence of the antibiotic for which resistance would indicate that expression had been achieved. (e.g. chloramphenicol, tetracycline, penicillin, kanamycin). Other techniques, such as spectrophotometric analysis for chloramphenicol acetyl transferase (CAT) are also complex and time consuming, require lysis or destruction of the bacteria being assayed, and are difficult to apply to the usual multitude of assay samples. See Goldfarb, et al, "Expression of Tn9-derived chloramphenicol resistance in *Bacillus subtilis*," *Nature* 293:309, 310 (Sept. 24, 1981); Williams, et al., "Cloning Restriction Fragments That Promote Expression of a gene in *Bacillus subtilis*," *J. Bact.* 146:1162 (June, 1981). The plasmids and methods of the present invention, however, provide means for identifying efficient promoters in DNA segments in a simple, rapid manner, with essentially immediately determinable results.

SUMMARY OF THE INVENTION

In accordance with the present invention, promoter probe vectors have been created which, when combined with effective promoter site-bearing DNA fragments, provide essentially immediate indication of foreign gene expression. The vectors of the present invention can be utilized to assay for promoter regions which are effective in both *E. coli* and *B. subtilis*, as well as other microorganisms. The vector contains an indicator gene which codes for production of a material which is immediately detectable and recognizable, preferably by color formation without lysis of the cells producing the product. Preferably the indicator gene codes for production of B-galactosidase, which can be readily detected in the medium by simple treatment with substances which change color when exposed to B-galactosidase, such as the chromogenic substrate XG, which is 5-bromo-4-chloro-3-indolyl-B-D-galactoside. See Davies et al., *J. Mol. Biol.* 36:413 (1968). In that way, those clones which contain plasmids resulting from combination of the vector of the present invention with a DNA fragment containing a *B. subtilis* promoter site region are readily identifiable by their blue color on the XG substrate.

Preferably, the probe vector has a number of restriction endonuclease attack sites, so that it can be cleaved with a number of different restriction endonucleases and still be functional when ligated to the DNA fragments of interest.

Another advantage of the vectors of the present invention is that they are essentially free of regulatory segments of DNA which may have been previously attached to the indicator gene. In contrast, the plasmid pPL603 utilized by Williams et al., supra, apparently still contains some elements of the regulatory sector it utilized in *B. pumilus* since the presence of some chloramphenicol is required in order to produce detectable amounts of CAT by the *B. subtilis* transformants which contain pPL603, and its derivatives. No such extraneous antibiotic is required to operate the probe vector of the present invention, or to induce expression of the indicator.

The probe vector of the present invention is particularly advantageous in programs for improvement of gene expression. For example, one way to improve gene expression is to locate an improved promoter segment for attachment to the gene. The very specific color reaction provided by the probe vector of the present invention permits (a) accurate comparison of the rate of expression of one plasmid with another plasmid; (b) selection of only those plasmids which achieve a chosen rate of expression; (c) selection of only those plasmids which show improved expression, as compared with their parent or sibling plasmids; (d) survival of only those microorganisms which exhibit a minimal, or improved, expression rate, etc. This can be particularly important in connection with programs to improve the expression, e.g. of plasmids which have previously established the ability to express the desired gene. For example, programs to improve expression by mutation of the DNA strands in the promoter region are substantially simplified by essentially immediate visual evaluation of each mutant, using the preferred probes of the present invention.

Another advantage to the present invention is that the probe can be utilized to test promoters in *E. coli* to select efficient ones before testing in *B. subtilis*. Aside from the fact that a promoter under investigation may be of considerable importance for its usefullness in *E. coli*, whether or not it is effective in *B. subtilis*, first expression in *E. coli* can be advantageous for other reasons. Typically, *B. subtillis* is only poorly transformable by DNA segments which have been ligated in a test tube. Moreover, *B. subtilis* normally requires dimerization of the plasmid under consideration in order to obtain expression. *E. coli*, on the other hand, does not require dimers, and expresses and replicates test tube plasmids with greater efficiency than *B. subtilis*. Transformation of plasmids into *E. coli* usually leads to production of plasmid dimers and other polymers, whicn can then be tested in *B. subtilis*.

Thus expression in *E. coli* of plasmids comprising a promoter or potential promoter sequence of interest ligated to the probe vector of the present invention provides (1) evaluation of the promoter sequence in *E. coli;* which information is also (2) confirmation of the existence of a promoter sequence in the DNA segment; (3) replication of the test plasmid for more effective testing; and (4) dimerization of the test plasmid to increase success in expression by *B. subtilis*.

Plasmids useful for introducing foreign DNA having a nucleic acid sequence which codes for production of a desired product into *B. subtilis* are double-stranded deoxyribonucleic acid molecules which preferably include a promoter DNA sequence which is derived from *B. subtilis* chromosomal DNA and a DNA sequence which is derived from a *B. subtilis* plasmid. Preferably, the promoter DNA sequence is derived from *B. subtilis* chromosomal DNA.

When foreign DNA coding for the production of a desired product is incorporated into these plasmids, additional plasmids useful for effecting expression in *B. subtilis* of the foreign DNA are formed. The resulting plasmids are double-stranded DNA molecules which include the foreign DNA, a promoter DNA sequence, preferably one derived from *B. subtilis* chromosomal DNA, and a DNA sequence derived from a *B. subtilis* plasmid.

The latter plasmids can be introduced into *B. subtilis* by transformation to produce genetically engineered bacterial cells which produce desired products when grown under suitable conditions. The products can then be recovered.

DETAILED DESCRIPTION OF THE INVENTION

Figure 1:
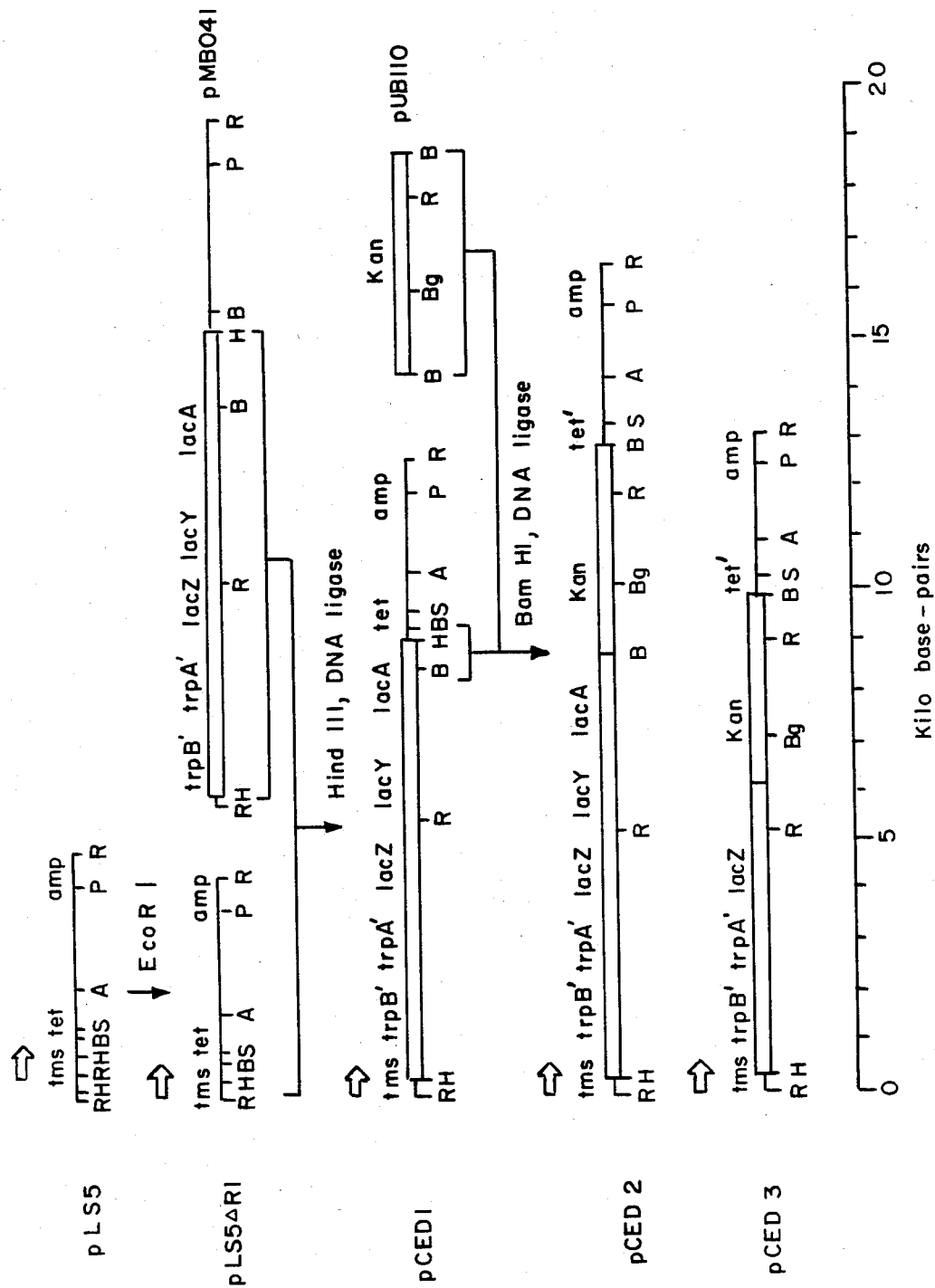
FIG. 1 shows the endonuclease restriction maps of various plasmids constructed in accordance with the teachings of this invention. Distances are measured from the EcoR1 site of pBR322. Abbreviations for restriction sites corresponding to restriction endonucleases are as follows: A-AvaI, B-BamH1, Bg-BglII, H-HindIII, P-PstI, R-EcoR1, S-SalI. These restriction endonucleases are commercially available products and, unless otherwise noted herein, are available from New England Bio Labs and/or Bethesda Research Laboratories, see, R. N. Davies, et al., Advanced Bacterial Genetics (Cold Spring Harbor, 1980), and are used in accordance with the instructions and conditions specified by their manufacturers.
Figure 2:
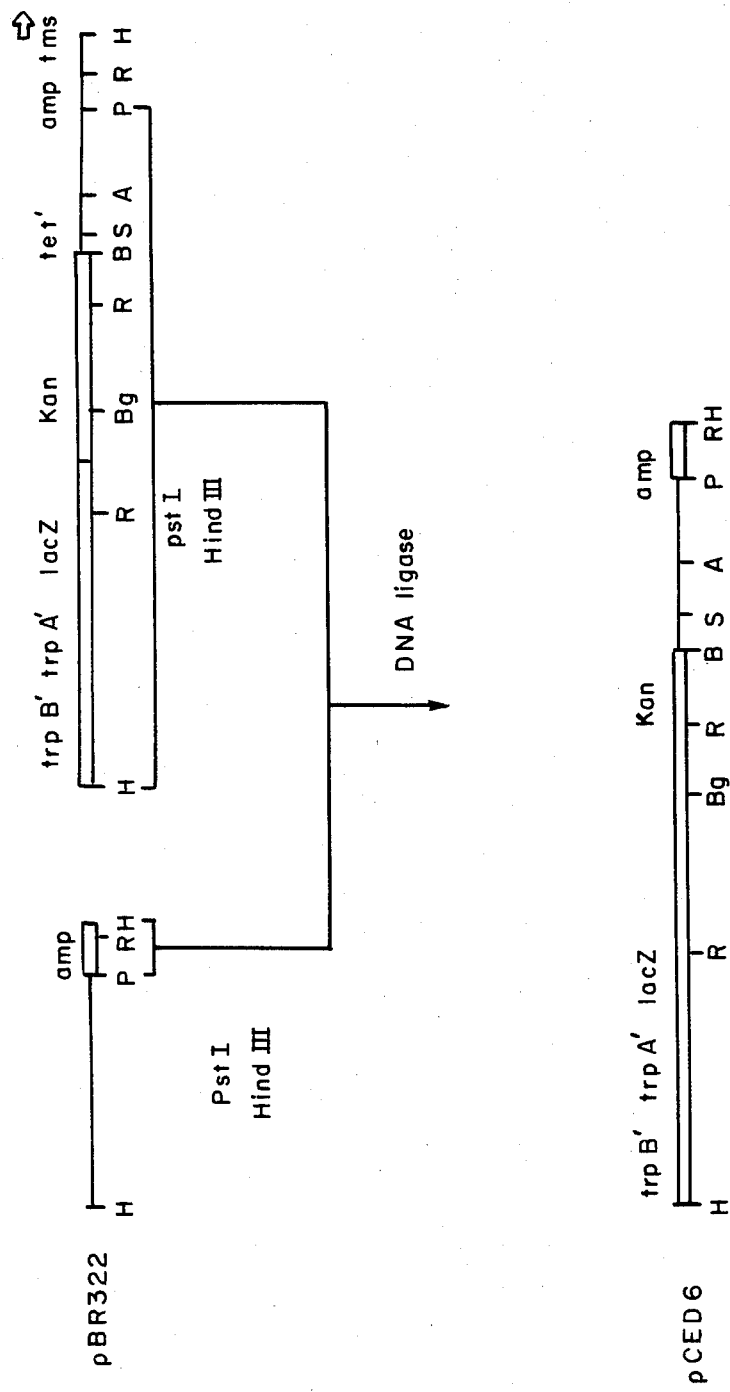
FIG. 2 shows the enconuclease restriction maps of further plasmids constructed in accordance with the teachings of this invention, including the plasmid pCED 6.

Plasmids have been constructed which are useful for the introduction into *B. subtilis* of foreign DNA which includes a gene or genes whose expression is associate with production of a desired products. The plasmids are double-stranded DNA molecules constructed in vitro by enzymatic means. They contain a relatively short DNA sequence necessary for activation of genes in *Bacillus subtilis*. The plasmids are of two broad types, those in which gene activation is stimulated during growth of the bacterial host, and those in which gene activation only occurs after growth ceases and sporulation begins. In the plasmids, the regulatory DNA is attached to longer sequences necessary for replication of the entire plasmid in *B. subtilis*, *E. coli*, or both.

Plasmids useful for introducing into *B. subtilis* of foreign DNA, the nucleic acid sequence of which codes for production of a desired product, are double-standed DNA molecules which include a promoter DNA sequence and the foreign DNA segment or gene.

The promoter DNA sequence may be derived from any source, the only limitation being its ability to function as a promoter when introduced into *B. subtilis* as part of a plasmid which also includes foreign DNA coding for a desired product. Suitable sources include other bacteria, e.g., *E. coli*, phage and viruses.

It has been found in the past that promoter candidates obtained from *B. subtilis* chromosomal DNA are more likely to operate as promoters in that organism than DNA from other sources. However, DNA segments from other sources can also function well as promoters in *B. subtilis*. Functional promoters have been derived from a 700 base pair Hind III fragment of *B. subtilis* chromosomal DNA which includes a promoter DNA sequence associated with the tms gene carried on *B. subtilis* chromosomal DNA. Additional information concerning *B. subtilis* chromosomal DNA and various promoters located thereon may be found in Haldenwang, W. G., et al., *J. Bacteriol.* 142:90–98 (1980) and Haldenwang, W. G., et al., *Cell* 23:615–624 (1981). In particular, FIG. 4 of the former publication shows a genetic and physical map of *B. subtilis* DNA which includes the 700 bp Hind III fragment. The disclosures of these publications are hereby incorporated by reference into the present disclosure to show the state of the art and to provide background information useful for a full understanding of this invention.

In some commercial applications, it may be desirable to have the foreign DNA coding for the desired product expressed during cell growth. In others, it may be preferable to have the foreign DNA expressed during sporulation, and some promoters are active in either phase. In each case, the promoter DNA sequence should be active during the desired period. It is therefore an aspect of this invention to provide promoter probe vectors which are effective in identifying promoters which are active during *B. subtilis* cell growth and/or during sporulation. Promoters which are active in one phase but not the other can be readily identified using the probe of the present invention.

The promoter probe vectors of this invention include the genetic information necessary for replication of the hybrid plasmid containing the gene of interest. Numerous suitable plasmids containing DNA which carries information necessary for replication in *B. subtilis* are available, including pUB110, pC194, pE194, pSA0501 and pSA2100.

Although the plasmids will typically be circular when used to transform *B. subtilis* cells, they may also be linear.

The foreign DNA having a nucleic acid sequence coding for production of a desired product may be derived from widely varying sources, including human, animal and plant sources, or it may be wholly or partially chemically synthesized. Examples of desired products, the genes for which may be used in the practices of this invention, include hormones, e.g., insulin, somatostatin and animal growth hormones, enzymes, antigens, vaccine components, e.g., viral coat proteins, and numerous other polypeptides.

The probe vectors, in accordance with the present invention, are made by using endonuclease and ligase enzyme treatments of known plasmids and chromosomal DNA segments to form a plasmid which contains the structural gene for B-galactosidase and which contains replicons for both *E. coli* and *B. subtilis*, but which does not contain any promoter for B-galactosidase which is recognized by *B. subtilis*. Preferably this is done by forming a plasmid which replicates in both *E. coli* and *B. subtilis*, and which expresses B-galactosidase when transformed into *B. subtilis*, and then excising the promoter which causes the expression of B galactosidase in *B. subtilis*. The *E. coli* and *B. subtilis* replicons may be obtained from known plasmids which replicate in *E. coli* and/or *B. subtilis*. A convenient source for B-galactosidase is the lac z segment of the lactose operon. See, e.g., M. Malamy, "Frameshift Mutations in The Lactose Operon of E. Coli," *Cold Spring Harbor Symposium on Quantitative Biology* 31:189 (1966), the disclosure of which is incorporated herein by reference. The source of lac Z is preferably pMB041 because it has a ribosome binding site properly positioned for B-galactosidase and that is known to be active in both *E. coli* and *B. subtilis*. See C. E. Donnelly, et. al., "Genetic Fusion of *E. coli* lac Genes to a *B. subtilis* Promoter," *Molecular Cloning and Gene Regulation in Bacilli* 63, 65 (Academic Press, Inc., 1982), the disclosure of which is incorporated herein by reference.

A preferred plasmid which has replicons for both *E. coli* and *B. subtilis* and which has demonstrated ability to express B galactosidase is *B. subtilis* plasmid pCED3. As described more fully hereinafter, pCED3 was derived from plasmid pCED2; which was derived from plasmids pUB110 and pCED1. Plasmid pCED1 in turn was derived from plasmids pLS5DR1 and pMB041. Plasmid pLS5DRI was derived from a known plasmid which contains an *E. coli* replicon, namely pBR322. See C. E. Donnelly, et al, supra.

The probe vectors of the present invention may be used by taking a source of the promoter of interest e.g., *B. subtilis* DNA, which may have numerous promoter regions, attaching a DNA segment having a promoter of interest upstream from the lac z gene in the probe vector, to form an operon fusion, transforming the fused promoter/vector into *E. coli* and/or *B. subtilis*, incubating the *B. subtilis*, and checking for the expression of a protein coded for by a genetic sequence contained in the probe vector.

The source of the promoter of interest used may be any source of DNA material which may act as a promoter in *B. subtilis*. For example, *B. subtilis* cells may be lysed and the chromosomal and/or plasmid DNA used as a source for the promoter region. Thus, DNA obtained from lysed *B. subtilis* cells may be cut with restriction endonuclease(s) to provide a number of DNA segments. Preferably a restriction endonuclease is used for which the promoter probe vector also has a restriction site at an appropriate location, so that the DNA segment(s) being evaluated can be ligated to the probe vector in a position which permits expression of an indicator gene from the vector. However, it is not absolutely necessary to utilize endonucleases that have appropriate restriction sites on the probe vector, since methods of chemically changing the ends of source DNA segments and/or the ends of the probe vector, so that the source DNA segments(s) and the probe vector can be ligated together, are well known in the art.

Other sources of potential promoters may also be used. For example, DNA segments from other species of microorganisms, animals or plants can be used to locate promoter segments which are capable of promoting expression in *B. subtilis*. Known promoters can be subjected to mutation by known means, e.g., chemical or radiological mutation, in order to improve their ability to express target genes in *B. subtilis* and/or *E. Coli*.

The promoter of interest should be attached upstream of the indicator gene in the probe vector. Normally at least some of the potential promoters will be attached to the probe vector in the appropriate location. However, where this does not occur, methods and means for changing the point of attachment are known and available in the art.

Preferably the attached probe vector and promoter of interest together form at least a part of a circular plasmid. However, it is possible to utilize the probe vector with attached test promoter region in the form of a linear DNA sequence or segment.

Methods and means are known for transforming *E. coli*, *B. subtilis* and other microorganisms with plasmids or other DNA segments. See e.g. Cohen et al., *Proc. Natl. Acad. Sci.* 69:2110 (1972); and Contente et al., *Molec. Gen. Genet.* 167:251 (1979), the disclosures of which are incorporated herein by reference.

Incubation of transformed cells is then carried on in appropriate media, with addition of suitable carbon source and other appropriate nutrients as required by the microorganism being incubated, as will be understood by the skilled in the art. Standard temperature and conditions are used. Preferably incubation is continued for a sufficient period of time to permit reasonable expression of the indicator protein and reasonable replication of the plasmids in the host cells. In that way, the efficiency of the promoter in expression of the desired protein, as well as the replicability of the plasmid or other vehicles which contain the promoter in the host microorganism, will both be evaluated.

Evaluations of the efficiency of expression requires analysis for the target protein, such as the enzyme B galactosidase. Where the expressed protein is secreted by the host cells, all that is necessary is testing of the supernatant fluid. The cells can be evaluated by contacting them with an evaluator for the target protein, e.g., the chromophoric indicator XG, discussed supra. Where the indicator protein is not secreted by the cells, the cells can be made more permeable, in order either to bring the indicator protein into the supernatant fluid, or to bring the evaluator substance into the cells. See e.g., J. Miller, *Experiments in Molecular Genetics*, e.g. at 352 (Cold Spring Harbor Lab. 1972); Fisher et al. "Ribonucleic Acid Synthesis in Permeabilized * * * Cells of *Bacillus Subtilis*," in *Spores VI*, p. 226 (Am. Soc. Microbiol. 1975), the disclosures of which are hereby incorporated herein by reference.

The term "indicator protein" is used to mean a substance, which, when expressed, can be detected by any of a variety of means. The preferred indicator protein of the present invention is the B-galactosidase enzyme, which can be readily detected in minute quantities by color indicators, as well as by a number of known assay techniques, such as a measurement of the ability to cleave o-nitrophenyl B-D-galactoside. See J. Miller, "Experiments in Molecular Genetics," supra. However, the probe vector may have other indicator proteins, which may be measured in a variety of ways. For example, the present probe vectors may carry the genes for resistance to certain antibiotics, e.g. for kanamycin resistance and ampicillin resistance. These types of markers are well known and permit self-selection of cells which achieve growth when such cells are grown in a medium containing bacteriostatic amounts of kanamycin and/or ampicillin.

The present invention encompasses a method of obtaining effective promoters for use in *B. subtilis* and *E. coli* using the promoter probe vector described above. This invention also encompasses the use of the promoter thus identified, together with some or all of the probe vector, to produce the desired results.

Once the promoter probe combination is discovered which leads to efficient expression and replication in the desired microorganisms, the gene coding for the product of ultimate interest (e.g. insulin, growth hormone, etc., hereinafter the "product protein") may be inserted into the promoter/probe sequence in expression relationship with the promoter, and the microorganism is then cultured or fermented to produce the product protein. Where it is not desired to co-express one, none or all of the indicator protein(s) with the product protein, the gene(s) for the unwanted indicator protein(s) are excised from the promoter/probe plasmid prior to expression.

Preferably the probe vector has at least one restriction site which can be used to insert the product protein gene into a position with respect to the promoter which will permit expression of that gene. That means that the product gene is inserted into the probe vector portion of the promter/probe combination at a point where the gene will be downstream from the promoter. Therefore, the promoter effectively governs and implements the expression of the product gene.

Preferably, the promoter probe vector has at least one endonuclease restriction site which can be used to place the product gene in close proximity to, and downstream from, the promoter segment. In the simplest case, for example, the product gene may be available in a form in which it is included in a DNA segment having endonuclease restriction sites upstream and downstream from the product gene. Preferably, the probe vector has at least one restriction site for the same enconuclease, at an appropriate location so that the product gene may be expressed under the influence of the promoter which the probe was used to find. If this is the case, the product gene can be inserted into the promoter/probe segment simply by cutting both the DNA segment which contains it and the promoter/probe sequence with the same restriction endonuclease, mixing the cut segments together, and ligating the parts together, followed by transformation into the microorganism of interest and selection of cells which produce the desired product. Where the product gene source and the promoter/probe segment do not share the same endonuclease restriction site, appropriate means and methods are known for cutting at other restriction sites, chemically building up appropriate sticky ends to patch the product gene into an appropriate location in the promoter/probe segment, and ligating the thus adjusted segments together.

In most cases, at least a portion of the probe vector will remain behind in the plasmid or other DNA segment which contains the promoter and the product gene. Where the segment of the probe vector which remains behind encompasses a complete gene (e.g. the kan gene) that gene will normally be expressed together with the product gene. Where the portion left in the chain does not encompass a complete gene, that portion will nevertheless function as a spacer in the DNA segment, spacing the product gene appropriately from the promoter to permit expression.

The plasmids and other vectors made and used in accordance with this invention may be prepared by methods known to those skilled in the art. Generally, they are constructed by enzymatic joining or ligation of the various DNA sequences under suitable conditions of temperature, time and the like. Similarly, methods are known for identifying, recovering and purifying the various DNA segments which are thereafter combined to form the plasmids; for transforming bacterial cells, including *B. subtilis*; for cloning transformed cells; and for recovering desired products, particularly polypeptides. The invention will be further illustrated by the following illustrative embodiments.

EXAMPLE 1

CONSTRUCTION AND EXPRESSION OF PLASMID pCED1 IN E. COLI

In the following examples, all restriction endonuclease digestions are carried out for 60 minutes at 37° C. and terminated by heating for 10 minutes at 65° C. Reaction conditions are those suggested by the suppliers of the enzymes. DNA fragments were ligated with T4 DNA ligase during incubation for 1-2 hours at room temperature or overnight at 13° C.

Plasmid DNA is purified from *E. coli* strains by the following method:

1. Grow 30 ml cultures in L Broth with antibiotic to select for plasmid carrying cells (at 37° C.);
2. Harvest cells at 10K (i.e. 10,000 RPM), 4° C. for 10 minutes in 50 ml screw cap Oak Ridge tubes;
3. Wash pellets with 5 ml of 0.05M Tris pH 8.0, vortex and spin at 10K, 4° C. for 10 minutes;
4. Resuspend pellets in 0.5 ml of 0.05M Tris pH 8.0 containing 25 percent sucrose. Transfer to small plastic screw cap tubes with Pasteur pipettes;
5. Add 0.12 ml lysozyme (5 mg/ml fresh), mix gently and incubate 5 minutes on ice;
6. Add 0.4 ml Triton Lysis Mix containing 100 ug/ml RNase (from 2 mg/ml, pre-heated stock) mixing gently while adding. Keep at 4° C.;
7. Spin at 20K, 4° C. for 60 minutes in SE12 rotor;

8. Remove supernatant by pouring into 13×100 glass screw-cap tube (should get about 1 ml);

9. Adjust volume to 2 ml with 0.05M Tris pH 8.0;

10. Add 2 ml of phenol (2x saturated with 0.05M Tris pH 8.0), mix gently to form emulsion and roll at 4°–6° C. for 25 minutes;

11. Separate phases at 4K, for 10 minutes at room temperature;

12. Remove lower phenol layer leaving behind any material at interface;

13. Add 2 ml fresh phenol and repeat step 10;

14. Separate phases; remove upper aqueous phase leaving behind interface and place in 20 ml snap-cap polypropylene tubes;

15. Extract 2x with 1.5 volumes ethyl ether (in hood). Mix and allow to settle each time before removing upper ether phase. Aqueous should change from very cloudy to clear as ether extraction continues;

16. to aqueous phase add 1/10 volume (0.2 ml) 3M sodium acetate and 4 ml of pre-chilled (−20° C.)95% ethanol. Mix well and leave for 60 minutes at −20° C.;

17. Spin at 10K, 4° C. for 20 minutes;

18. Discard supernatant; rinse (do not resuspend) pellet with 2 volumes cold 95 percent ethanol, then place at −70° C. for 1 hour;

19. Repeat steps 17 and 18. Remove last traces of ethanol by placing in vacuum lyophilizer. Replace caps and punch hole in center before placing tubes in desiccator; and 20. Dissolve DNA in 0.1 ml of TE80 and store at 4° C.

The formula for the Triton Lysis Mix (50 ml) is as follows:

| | |
|---|---|
| 0.3% Triton X100 | 0.15 ml stock Triton X100 |
| 0.15 M Tris pH 8.0 | 7.5 ml 1 M Tris pH 8.0 |
| 0.18 M Na$_2$ EDTA | 36.0 ml 0.25 M EDTA, pH 8.0 |
| | 6.35 ml H$_2$O |
| | 50.0 ml |

The formula for L Broth is as follows:
10 g Tryptone (Difco)
5 g Yeast extract (Difco)
5 g NaCl
1 l. water
pH adjusted to 7.0 with NaOH The formula for TE 80 is 30 mM Tris/HCl, pH 8.0, and 5 mM EDTA.

Plasmid DNA was purified from *B. subtilis* strains by the method of Gryczan, T. J. et al., *J. Bacteriol* 134:318 (1978). In all cases, the purification was followed by equilibrium density gradient centrifugation in cesium chloride containing ethidium bromide.

Known methods of transformation of bactrial cells by plasmid DNA were followed. Calcium chloride-treated cells of *E. coli* cells were transformed with plasmid DNA or ligated DNA as described by Cohen, S., et al., *Proc. Natl. Acad. Sci.*, U.S.A. 69:2110 (1972). Competent cells of *B. subtilis* were prepared as described by Contente, S. and Dubnau, D., *Molec. Gen. Genet.* 167:251 (1979). Antibiotic-resistant transformants were selected after 1.5 hours of growth after exposure to DNA in antibiotic-free medium. Drug concentrations used were per ml 10 ug ampicillin, 10 ug tetracycline and 5 ug kanamycin. (In this application u means mu, or micron, B means beta, and D means delta.

Two alternate methods were used to determine the amount of B-galactosidase produced by transformed cells. One method involved the analysis for B-galactosidase in permeabilized cells. *E. coli* cells were made permeable by treatment with CHCl$_3$ and sodium dodecyl sulfate (SDS) according to Miller, J., *Experiments in Molecular Genetics*, p. 352 (Cold Spring Harbor Lab., 1972). Permeable cells of *B. subtilis* were prepared by the cold Tris-toluene method of Fisher, S., et al., in *Spores VI* p. 226, (Am. Soc. Microbiol., (1975).

The second method used was to assay extracts of lysed cells for B-galactosidase content. To make extracts, cultures were concentrated 100-fold in PM2 buffer, containing phenylmethylsulfonyl fluoride and sonicated for 3–6 minutes in a beaker with a jacket through which ice-salt water was continually passed. The sonicate was centrifuged for 1 hour at 100,000 xg. The supernatant fluid was assayed for B-galactosidase activity.

B-galactosidase was assayed by cleavage of o-nitrophenyl B-D-galactoside by the method of Miller, J., supra. One unit of activity produces an increase in absorbance at 420 nm of 1.0. Activity is expressed in units per milligram protein. For whole cell assays, total cellular protein was measured.

A more rapid, visual determination of B-galactosidase activity (LacZ+ phenotype) was to use the chromophoric material XG. *E. coli* and *B. subtilis* strains were assayed for LacZ phenotype on L agar containing 5-bromo-4-chloro-3-indolyl-B-D-galactoside (XG; J. Davies, et al and *J. Mol. Biol.* 36:413 (1968)). LacZ+ colonies are blue, LacZ- colonies are white. To test the LacY phenotype of *E. coli* strains, they were plated at 42° C. on MacConkey Agar containing melibiose, see L. S. Prestidge, et. al., *Biochim. Biophys, Acta.* 100:591 (1965)]. Milibiose is transported by the lac permease. LacY+ colonies are red; LacY- colonies are light pink or white.

To construct a plasmid useful for creating operon fusions, the promoter region of the tms gene (a gene identified by a mutation which causes growth to be temperature sensitive, see J. C. Copeland, et al., *Bact. Rev.* 32:301 (1968)) was cloned as part of a 700 base pair Hind III fragment of *B. subtilis* DNA that was ligated to Hind III-cut pBR322. pBR322 is a known cloning vector which produces a substantial resistance to tetracycline and ampicillin in *E. coli*. See Sutcliffe et al., *Cold Spring Harbor Symposium on Ouantatative Biology* 43:77 (1979), the disclosure of which is incorporated herein by reference. The 700 bp fragment was derived from p63, another known plasmid. See K. W. Hutchinson, et al. *Gene* 8:267 (1980) and W. G. Haldenwang et al., *Cell* 23:615 (1981), the disclosures of which are incorporated hereby in reference.

The resultant plasmid, pLS5 (shown in FIG. 1) was then digested with EcoR1 and transformed into *E. coli*, selecting for ampicillin-resistance. The deletion plasmid that resulted, termed pLS5DR1 (also shown in FIG. 1), has a single Hind III site known to be 85 bp downstream from the tms start point for transcription. See Haldenwang, et al., supra. A Hind III fragment containing the lac Z Y and A genes, but no promoter site for these genes, existed on pMB041, a phenotypically Lac− plasmid. pLS5DR1 and pMB041 plasmid DNAs were digested with Hind III, ligated, and used to transform *E. coli* strain RV (Delta lac). Ampicillin resistant transformants were selected on plates containing the chromogenic substrate XG (as described above). Blue colonies that appeared (i.e. they were LacZ+—they produced B-galactosidase) were screened for the presence of the pLS5D R1-lac hybrid plasmid. A transformant was isolated which harbored a plasmid, pCED1 (shown in FIG. 1), in which the lac genes were inserted downstream of the tms promoter. E. coli cells carrying pCED1 grew well on minimal medium with lactose as sole carbon source, indicating reasonably high level expression of the lac genes.

Direct assay of the B-galactosidase activity indicated the pCED1 was able to direct synthesis of high amounts of the enzyme. The yield was about 2.3 units per milligram of protein for B-galactosidase measured in the supernatant fluid from permeabilized cells, and about 20 units per milligram protein for measurements of the extract from lysed cells. For comparisons, cells carrying pCED1 have a 30-fold higher specific activity than those carrying pMB401, the promoter-less version of the same lac DNA. This high activity is comparable to that provided by pMB040, a pBR322 derivative in which the lac genes are driven by the efficient lac UV5 promoter. A restriction endonuclease map of pMB041 corresponds to that of pMB040 shown in FIG. 1, except that pMB040 has an added EcoR1 fragment of 205 bp. This fragment originated in the E. coli chromosome from a mutant strain (UV5) that shows unregulated expression of the lac operon. This fragment is from the E. coli lac regulatory region. Additional information may be found in A. E. Silverstone, et al., *Proc. Natl. Acad. Sci., U.S.A.* 66:773 (1970). The finding of 2.3 units per mg protein for RV(pCED1), as measured with permeable cells, is equivalent to an activity of 350 units per ml culture in the standard assay of J. Miller, *Experiments in Molecular Genetics* (Cold Spring Harbor Laboratory, (1972).

pCED1 (Lac+) is identical to pMB041 (Lac−) except that a 29 bp EcoR1-Hind III segment has been replaced by a corresponding 280 bp segment of *B. subtilis* DNA. This provides circumstantial evidence that the tms promoter is able to direct lac expression in *E. coli.* When the lac DNA was inserted into pLS5DR1 in the orientation inverse to that of pCED1, a Lac+ phenotype was also observed, suggesting that a promoter site of pBR322 directs transcription leftward from the region of the tet genes. This is confirmed by the fact that inverting the lac-pBR322 orientation of pMB041 leads to the Lac+ phenotype and by the direct observation by Stuber, D. and Bujard, H., *Proc. Natl. Acad. Sci.*, 78:167 (1981) of a transcription initiation site near the beginning of the tet genes, from which RNA is copied from the anti-sense strand of the tet sequence.

pBR322, the cloning vector from which pLS5 was derived, normally determines resistance to at least 25 ug tetracycline per ml. Since in constructing pLS5, *B. subtilis* DNA was cloned into the Hind III site of pBR322, a site located within the promoter region for the tet genes, it is not surprising that pLS5-containing strains are only resistant to 10 ug tetracycline per ml. The subsequent deletion that formed pLS4DR1 removed 29 bp of pBR322 DNA and 420 bp of *B. subtilis* DNA. This led to an unexpected increase in the level of tetracycline-resistance. *E. coli* cells carrying pLS5DR1 are resistant to 25 ug tetracycline per ml. A possible explanation is that the deletion brought together DNA sequences which act as a new promoter for transcription of the tet genes.

Alternatively, the deleted DNA may have contained a termination sequence or a sequence inhibitory to tms expression. After insertion of lac DNA between the tms promoter and tet, the level of resistance determined dropped to 10 ug/ml. These perturbations in the level of tetracycline-resistance prevent one from concluding that the only source of lac expression in pCED1-carrying cells is the tms promoter.

pCED1 does not replicate in *B. subtilis*, although it contains a 280 bp sequence of DNA from the *B. subtilis* genome. This homology was apparently insufficient to generate recombination events that would lead to plasmid integration into the *B. subtilis* chromosome. Even in a congression experiment in which competent cells were exposed to 10 ug of pCED1 DNA, any LacZ+ colonies were unable to be detected among transformants.

EXAMPLE 2

Construction and Expression of Plasmid pCED2

Because plasmid pCED1 did not replicate in *B. subtilis*, the tms-lac operon was cloned onto pUB110, a high copy number plasmid which replicates in *B. subtilis*. pUB110 contains one BamH1 site; linearized pUB110 (4400 bp) was exchanged for the small BamH1 fragment (1100 bp) of pCED1, creating pCED2 (shown in FIG. 1). The kanamycin resistance coded for by pUB110 is expressed in both *B. subtilis* and *E. coli*. All kanamycin resistant transformants of *E. coli* were ampicillin resistant, Lac+, and Tet$^S$. The latter was expected since part of the coding sequence of tet was removed.

Transformation of plasmid pCED2 into *E. coli* strain RV produced a stable transformant with high B-galactosidase production. (2.3 units per mg protein from solubilized cells, 15 units per mg protein in the extract). When pCED2 was transformed into *B. subtilis*, many of the initial Kan$^r$ transformants were LacZ+ (i.e., blue on XG plates). When these transformants were purified, however, they provided to segregate Lac− cones at very high frequency. Plasmid DNA isolated from such unstable transformants was of variable size, but was always less than that of pCED2. If transformants were purified on non-selective medium (i.e., without kanamycin), the plasmid was lost completely.

EXAMPLE 3

Construction and Transformation of Plasmid pCED3

It was thought that pCED2 might be stabilized in *B. subtilis* strain CB20 (Haldenwang, W. G., et al., *J. Bacteriol.* 142:90 (1980)), the disclosure of which is incorporated herein by reference. This strain contains in its chromosome an integrated plasmid that has some homology with the pBR322 component of pCED2. Transformation of this strain with pCED2, however, also resulted in Lac+ colonies that segregated Lac− derivatives at high frequency. However, repeated subculturing of the Lac+ colonies led eventually to the isolation of a stably Lac+ derivative. Restriction analysis of the plasmid DNA of one of these stable transformants showed that a deletion had occurred. The deletion plasmid, termed pCED3, had lost about 3 Kb of DNA at the junction of pUB110 and the lac genes (see FIG. 1). When pCED3 was transformed into *E. coli* strain RV, the resultant transformants were phenotypically LacZ+LacY−. The deleted DNA starts beyond the EcoR1 site within the lacZ gene, extends through the lacY and A genes, and ends within the pUB110 sequence.

The presence of chromosomal homology in strain CB20 was apparently of no consequence in the stabilization of pCED3. Transformation of pCED3 into *B. sub-*

*tilis* strain BR151 gave fully stable transformants. The stabilization seems more likely to derive from the deletion removing a DNA sequence that is harmful to *B. subtilis*. Although *B. subtilis* strains harboring pCED3 are stably Lac+ on plates containing kanamycin, they show rapid loss of both Lac+ and Kan$^r$ phenotypes when grown in the absence of the drug.

Assay for B-galactosidase production for *B. subtilis* strain BR151 transformed with plasmid pCED3 showed levels of 1.5 and 2.0 units per mg proteins for analysis of (a) supernatant from permeabilized cells and (b) extract from lysed cells, respectively. Comparative analysis for *B. subtilis* BR151 untransformed and BR151 transformed with plasmid pUB110 failed to generate as much as 0.01 units per mg protein, as measured by either testing method. It is clear that the presence of pCED3 leads to high-level expression of B-galactosidase in *B. subtilis*. No detectable activity was found in cells without plasmid or in cells carrying pUB110. Because of a report [Caulfield, M. P. et al., *J. Bacteriol.* 138:345 (1979)] that a strain of *B. subtilis* designated 1007 had a B-galactosidase activity inducible by lactose, a search for such activity in BR151 was conducted. No such activity was found.

In vitro transcription studies of the tms region indicate that the tms gene is only transcribed by the major RNA polymerase present in vegetative cells [Haldenwang, W. G., et al., Cell 23:615 (1981)]. RNA polymerase molecules containing sigma factors that recognize sporulation genes in vitro do not initiate transcription effectively from the tms promoter. By assaying B-galactosidase in the fusion strain during growth and sporulation, it was found that B-galactosidase activity decreased five-fold by $T_2$ (Table I). Activity was measured in extracts of sonicated cells to avoid the possibility of differential permeabilization of vegetative and sporulating cells. The amount of soluble protein liberated by sonication was constant for each sample taken after $T_0$. The decrease in B-galactosidase activity during sporulation is consistent with the idea that the tms promoter is only poorly active after the end of growth, and the B-galactosidase protein is subject to normal sporulation-associated protein turnover.

TABLE 1

| \multicolumn{2}{c}{EXPRESSION OF B-GALACTOSIDASE IN GROWING AND SPORULATING CELLS OF BR151 (pCED3)} | |
| --- | --- |
| Time of harvest | Unit of B-Galactosidase activity per mg protein |
| $T_{-2}$ | 3.0 |
| $T_0$ | 1.4 |
| $T_1$ | 1.1 |
| $T_2$ | 0.6 |

Thus, construction of plasmids in which protein coding sequences from *E. coli* have been inserted downstream from a *B. subtilis* promoter site has been accomplished.

EXAMPLE 4

Construction of Plasmid pCED6

Since the spontaneous lacY-lacA deletion carried by pCED3 had established stability of transformants of that plasmid into *B. subtilis*, we sought to create a promoter-less plasmid that would carry that deletion. This was accomplished simply by cutting pCED3 and pMBO41 each with endonucleases PstI and Hind III. Upon mixing the fragments with DNA ligase and subsequent transformation of *E. coli* RV, we isolated clones that were ampicillin-resistant, kanamycin-resistant and lacZ−. That would only occur if a recombinant had arisen that contained the deleted version of the lac genes from pCED3 but did not contain that *B. subtilis* tms promoter present on pCED3. By restriction mapping, the structure of pCED6 was verified. It was shown to transform *B. subtilis* efficiently and to give rise to stable clones carrying a plasmid identical to pCED6 isolated from *E. coli*. A sample of *E. coli* RV cpontaining plasmid pCED6 has been deposited at the American Type Culture Collection, under the accession number 39279.

EXAMPLE 5

Confirmation of Promoter Activity

A known promoter fragment for the "0.4Kb" *B. subtilis* gene which is only expressed during sporulation, was inserted into the Hind III site of pCED6. The promoter segment did not have Hind III restriction sites at both ends, so a short DNA segment having that recognition site was added to the ends before insertion into pCED6. The new plasmid (pCED7) was used to transform *B. subtilis*, and was successful in stimulating production of B-galactosidase during sporulation. This confirmed the ability of the promoter probe vector pCED6 to recognize promoters useful in inducing product expression by *B. subtilis*.

EXAMPLE 6

Location of Promoter from Glutamate Synthase Gene

A plasmid carrying at lesat a part of the glutamate synthase (gltA) gene of *B. subtilis* was constructed. After cleavage with Hind III, fragments were ligated to pCED6 that had also been cut with Hind III, and used to transform *E. coli* RV and *B. subtilis* BR 151. Clones of both *E. coli* and *B. subtilis* were isolated in which B-galactosidase activity was detected when incubated on XG medium. These clones proved to have a 1.9 kb Hind III fragment from the gltA region inserted into pCED6. This 1.9 kb, Hind III fragment contained a promoter segment which was used for the first time in *B. subtilis* to produce B-galactosidase via the promoter probe plasmid pCED6 of the present invention.

EXAMPLE 7

Location of Promoter From Aconitase Gene

A plasmid carrying at least part of the aconitase (citB) gene was constructed. As in Example 8 above, Hind III fragments of this plasmid were ligated to pCED6. At least one fragment proved to cause expression of B-galactosidase in both *E. coli* and *B. subtilis*.

The specific embodiments described herein are meant to be exemplary only, and various modifications will be apparent to those skilled in the art. The claims below are intended to cover all such modifications.

What is claimed is:

1. A promoter probe vector, comprising a replicon active in *Escherichia coli*, a replicon active in *Bacillus subtilis*, a structural gene for B-galactosidase, and at least one endonuclease restriction site suitable for insertion of promoter-containing fragments of DNA.

2. The vector of claim 1, wherein the replicon active in *Escherichia coli* comprises a replicon obtained directly or indirectly from plasmid pBR 322, and wherein the vector is useable to identify promoter sequences which are active in both *Escherichia coli* and *Bacillus subtilis*.

3. The vector of claim 1, wherein the replicon active in *Bacillus subtilis* comprises a replicon obtained directly or indirectly from plasmid pUB110.

4. The vector of claim 1, wherein the structural gene for B-galactosidase is the lacZ gene from *Escherichia coli*.

5. The vector of claim 1, wherein the endonuclease restriction site is a cleavage site for at least restriction endonuclease selected from the group of AvaI, BamHI, BglII, HindIII, PstI, EcoR1 and SalI.

6. The vector of claim 1, said vector having the properties of pCED6.

7. The vector of claim 6, said vector being pCED6, or a derivative or mutant thereof.

8. The vector of claim 1, said vector further carrying the structural gene for at least one type of antibiotic resistance.

9. A method of testing DNA segments for the presence of a promoter, comprising inserting the DNA segments into a promoter probe vector to form a test plasmid, which vector comprises a replicon for *Escherichia coli*, a replicon for *Bacillus subtilis* and a structural gene for B-galactosidase, transforming *Escherichia coli* or *Bacillus subtilis* with the test plasmid, and analyzing the products made by the transformant for B-galactosidase.

10. The method of claim 9, wherein *Escherichia coli* is first transformed with the promoter probe vector containing the promoter, and then *Bacillus subtilis* is transformed with the promoter probe vector containing the promoter, and the analysis for B-galactosidase is carried out by contacting the bacteria with a substance which undergoes a color change in the presence of B-galactosidase.

11. The method of claim 10, wherein the substance used to analyze for B-galactosidase is 5-bromo-4-chloro-3-inodolyl-B-D-galactoside, or o-nitrophenyl-B-D-galactoside.

12. A method of constructing a plasmid for use in expression of a product by *Bacillus subtilis*, said product being encoded by a product gene, comprising:

(a) identifying a promoter useful for promoting expression of genetic products by *Bacillus subtilis* by (1) inserting promoter DNA segments into a promoter probe vector to form a test vector, said probe vector comprising a replicon for *Escherichia coli*, a replicon from *Bacillus subtilis* and a structural gene for B galactosidase, (2) transforming *Escherichia coli* or *Bacillus subtilis* with said test vector to form at least one transformant, and (3) recovering the promoter-containing test vector from at least one transformant which produced B-galactosidase;

(b) forming a production vector by inserting a structural gene which codes for the desired product in the test vector;

(c) transforming *Bacillus subtilis* with the production vector;

(d) incubating the transformed *Bacillus subtilis* under conditions which permit production of the desired product, and (e) recovering the desired product.

13. The method of claim 12, wherein the probe vector is a plasmid having the properties of pCED6 or a derivative thereof.

14. The method of claim 13, wherein the probe vector is the production vector produced by the method of claim 12.

* * * * *